United States Patent [19]

Hodakowski et al.

[11] Patent Number: 5,429,230

[45] Date of Patent: * Jul. 4, 1995

[54] CONTAINERIZATION SYSTEM FOR AGROCHEMICALS AND THE LIKE

[75] Inventors: Leonard E. Hodakowski; Chi-Yu R. Chen; Samuel T. Gouge, all of Raleigh; Paul J. Weber, Durham, all of N.C.

[73] Assignee: Rhone-Poulenc, Inc., Research Triangle Park, N.C.

[*] Notice: The portion of the term of this patent subsequent to Jan. 14, 2009 has been disclaimed.

[21] Appl. No.: 150,500

[22] Filed: Nov. 10, 1993

Related U.S. Application Data

[63] Continuation of Ser. No. 54,327, Apr. 28, 1993, Pat. No. 5,328,025, which is a continuation of Ser. No. 818,110, Jan. 8, 1992, Pat. No. 5,248,038, which is a continuation-in-part of Ser. No. 554,615, Jul. 18, 1990, Pat. No. 5,080,226.

[51] Int. Cl.$^6$ ............................................. B65D 85/82
[52] U.S. Cl. ............................... 206/205; 71/DIG. 1; 252/315.1; 424/409; 206/524.7
[58] Field of Search ............ 71/DIG. 1; 206/0.5, 206/205, 219, 484, 521, 524.1, 524.6, 524.7; 252/315.1; 383/109, 113; 424/409, 412; 514/801, 944

[56] References Cited

U.S. PATENT DOCUMENTS

| | | | |
|---|---|---|---|
| 3,695,989 | 10/1972 | Albert | 206/524.7 |
| 3,892,905 | 7/1975 | Albert | 206/524.7 |
| 4,681,228 | 7/1987 | Kerry et al. | 206/484 |
| 4,846,992 | 7/1989 | Fonsny | 206/524.7 |
| 4,885,105 | 12/1989 | Yang et al. | 206/524.7 |
| 5,080,226 | 1/1992 | Hodakowski et al. | 206/524.7 |

FOREIGN PATENT DOCUMENTS

| | | | |
|---|---|---|---|
| 0471800 | 1/1972 | Japan | 206/524.7 |
| 0013504 | of 1912 | United Kingdom | 206/524.7 |
| 0922317 | 3/1963 | United Kingdom | 206/524.7 |
| 8912587 | 12/1989 | WIPO | 206/524.7 |

*Primary Examiner*—Jimmy G. Foster

[57] ABSTRACT

This invention relates to a containerization system and to containers which are particularly suitable for storing, packaging and transporting toxic or hazardous products, such as agricultural chemicals. The containerization system comprises the chemical in the form of a gel which is contained within a water-soluble or water-dispersible bag.

1 Claim, No Drawings

CONTAINERIZATION SYSTEM FOR AGROCHEMICALS AND THE LIKE

This is a continuation of application Ser. No. 08/054,327 filed Apr. 28, 1993, now U.S. Pat. No. 5,328,025, which is a continuation of Ser. No. 07/818,110 filed Jan. 8, 1992, U.S. Pat. No. 5,248,038, which is a continuation-in-part of U.S. Ser. No. 07/554,615 for "Containerization System for Agrochemicals and the Like" filed Jul. 18, 1990, now U.S. Pat. No. 5,080,226. This application is filed by the same inventors named in U.S. Application Ser. No. 07/554,615, U.S. Pat. No. 5,080,226, incorporated herein by reference.

FIELD OF THE INVENTION

This invention relates to a containerization system and to containers which are particularly suitable for storing, packaging and transporting toxic or hazardous products, e.g., agricultural chemical compounds, such as pesticides.

BACKGROUND AND PRIOR ART

At present, most hazardous and toxic liquids are stored in metal drums or, where smaller quantities are involved, in plastic containers. Hazardous or toxic compounds, such as agrochemical compounds, are formulated in various compositions.

The expression toxic or hazardous compounds as used herein means an industrial chemical or agrochemical compound, which, if released in the quantity or concentration normally present in storage and shipping containers, may cause damage to the environment or be injurious to a person contacted by it.

With respect to agricultural chemicals, liquid compositions, particularly in the form of concentrates, are most convenient for farmers because of the relative ease with which they can be handled, formulated and used. However, there are significant difficulties in handling such liquid compositions.

There is a danger of spillage or leakage if holes develop in the containers or if containers are accidentally dropped and thereby crack or fail. Containers have been developed which possess great resistance to impact and shock. While such containers are secure under normal storage and handling conditions, in the event of an accident, for example during transporting, there remains an appreciable risk of spillage or leakage with rapid loss of liquid. Leakage of toxic and hazardous chemicals can create damage to the environment.

The chemical and packaging industries have long sought a secure container which provides sufficient safeguards for those handling it, such as farmers and transporters, as well as adequate protection for the environment.

It is known, for example, to package agrochemicals in soluble bags or sachets made from films. However, such films may crack and break and thus cause leakage of the agrochemical contents. There are a variety of defects which can occur in films, which may lead to weaknesses of the film and become a potential source of leakage. For example, the presence of air bubbles, dust particles or foreign bodies in gel particles or the existence of thin points on or in the film are all potential weak points. If a film with such a weak point is subjected to a lot of handling or physical shock, the film may fail at a weak point. This is especially a problem in the agrochemical industry where containers may be subjected to repeated and uncontrolled handling by distributors, transporters or farmers.

In other industries such as pharmaceuticals and cosmetics, gel formulations have been used as a means for packaging pharmaceutical or cosmetic products. However, such gel formulations are often utilized for aesthetic and other reasons and not as part of a containerization system for holding and securing toxic or hazardous chemicals. Furthermore, the gels used for pharmaceutical or cosmetic purposes are generally water-based.

Another possibility is to provide agrochemicals in the form of wettable powders which can be contained within a bag which may be water soluble or water dispersible. However, when wettable powders are placed in water soluble bags and then added to water in spray tanks, the bag floats because the bulk density of the product is low. As the bag floats in the spray tank, it can become attached to either the side of the tank or recirculation piping within the tank. This is because the materials used in water soluble bags, such as polyvinyl-alcohol, tend to be sticky and become a very good adhesive when wet. The longer it takes to get the bag to dissolve, the higher the probability that the bag will adhere to some part inside the spray tank. Another problem is that as the bag dissolves and releases the powder, some powder gets bound to the bag and does not disperse. Also, in view of its relatively low density, the bag floats above the water level in the tank which further inhibits full dissolution of the bag. This problem can build up over time and cause numerous problems due to filters getting clogged by either undissolved bag or wettable powder that has not been properly wetted and which becomes stuck to the filter system of the spray tank or the spray nozzles. This causes serious problems since the farmer/applicator must clean this up, potentially exposing himself to the chemical itself.

Also suggested have been containing systems for pesticides in which the liquid-containing active ingredient is enclosed within soluble bags or sachets. However, the bags tend to develop pinholes and the contained liquid leaks under such conditions causing potential injury to the environment.

It has also been proposed for pesticides to be packaged in soluble bags or sachets which contain an air space to absorb shocks and to avoid leakage. This feature does tend to reduce bag failure. However, this does not avoid the problems of pinholes. Also, this approach has a disadvantage in that such bags cannot effectively be used as a self-dispensing container. The specific gravity of liquid and the included air space, causes such a bag to float and not to become immersed when placed in a spray tank. As a result, there is incomplete contact between water and the bag which is not adequate for rapid dissolution.

SUMMARY OF THE INVENTION

The present invention provides a containerization system comprising a water soluble or water dispersible bag which encloses, holds and secures a chemical compound which can be a toxic or hazardous chemical; the chemical compounds is present in a gel which is of essentially organic material. The present invention is also directed to a containerization system that can self-dispense the active ingredient contained therein when placed in an aqueous medium. The present invention also concerns a method for holding and securing chemicals in a manner which reduces the chances of the chemical spilling, leaking or contacting with the environment during shipping and storage.

An object of the instant invention is to provide a new method and system for storing, containing and packaging toxic and hazardous compositions such as agrochemicals which is safe for handling.

Another object of the instant invention is to provide a new system to contain agrochemicals which is easy to manipulate for the farmer.

Another object of the instant invention is to provide a new system for containing chemicals such as agrochemicals which enables such chemicals to be readily, rapidly and easily solubilized and/or dispersed in water, preferably in less than five minutes under normal agitation.

Another object of the instant invention is to provide a new system for storing, containing and packaging chemicals such as agrochemicals, said system utilizing a minimum amount of volumetric space.

Another object of the instant invention is to provide a new container and a new system for containing hazardous compounds which diminishes the risks of leakage and pollution.

Another object of the instant invention is to avoid leakage through pinholes of a bag containing hazardous compositions. Only one pinhole among thousands of bags is enough to cause a lot of trouble, because the liquid going through the pinhole contaminates all of its environment.

Another object of the instant invention is to avoid breakage of the container with its contents. When the container is rigid, there is substantial possibility of simple breakage. With a liquid in a bag this possibility is somewhat reduced, but the liquid still transmits the shocks and there is the problem of hydraulic hammer effect. An object of the instant invention is to avoid this hydraulic hammer effect. It has been proposed to reduce the possibility of breakage by means of an air space in the bag, but this represents some loss of storage space.

Another object of the present invention is to dissipate, as much as possible, the force of a shock to a container.

Another object of the present invention is to provide a shock absorbing system for containing agrochemicals, e.g., pesticides.

A further object of the present invention is to provide a containing system wherein less solvent is needed in the formulation of the chemical, which is a cost saving advantage both in shipping and manufacturing.

An additional advantage of the present invention is that higher concentrations of active ingredient can be obtained when using gels rather than liquids.

The present invention seeks to provide a new container system for agrochemicals which quickly dissolves when put into water. The invention further seeks to provide a new container system for agrochemicals which reduces the risk of clogging the spray nozzles or the filters of spray tanks.

Other objects and advantages of the invention will be apparent from the description which follows. Other objects of the invention will better appear from the following description. The objects of the invention can be achieved in full or in part by means of the invention.

DESCRIPTION OF THE PREFERRED EMBODIMENTS

The containerization system of the present invention comprises a bag composed of a water soluble or water-dispersible film which envelops and encloses a hazardous or toxic chemical present in a gel. The gel provides its own discrete advantages and applications as a concentrate for the chemical compound. When the gel of the present invention is used in conjunction with the enveloping bag, a containerization system is provided which is unique in its ability to maintain integrity and prevent leakage of the subject chemical into the environment.

The ultimate purpose of the containerization system is to preserve a toxic or hazardous chemical in a form which can be safely handled and which is secured in a manner preventing its rapid leakage into the environment. The invention achieves these objectives not merely by creating an enveloping barrier of protection but by employing a system integrally related to the subject chemical.

The present invention also includes a method for holding and securing chemical compounds, such as toxic and hazardous compounds, in a manner to prevent their contact with the environment during shipment and storage.

As already explained, a toxic or hazardous chemical can be any compound which can cause injury to persons exposed to the chemical or which can damage the environment. One class of such compounds is agricultural chemicals or agrochemicals such as pesticides (e.g., herbicides, fungicides, nematocides, insecticides, etc.) and plant protection agents (e.g., plant growth regulators, nutrients, etc.).

In practice, the gel material used in the invention comprises the active ingredient, which is the hazardous or toxic chemical in association with ingredients that participate in or assist in the formation of the gel, for example, surfactants, dispersants, thickeners, solvents and gelled or gelling agents.

A gel is generally a colloid in which the dispersed phase has combined with the continuous phase to produce a viscous, jelly-like product. A gel can be a dispersed system consisting typically of a high molecular weight compound or aggregate of small particles in very close association with a liquid. The gels used in the invention usually have an organic continuous phase, in contrast to most existing gel materials which are water-based and have an aqueous continuous phase. Furthermore, the gels used in the invention have essentially one physical phase, at least as can be seen when visually observed. Gels that are preferred for the invention are those which can be divided by cutting and whose cut parts are able to merge together by simple juxtaposition.

Solvents useful in the gel of the present invention are organic solvents such as petroleum hydrocarbons which include aliphatic and aromatic solvents. Surfactants that can be used in the invention are nonionic and anionic surfactants and combinations thereof. Illustrative gelling agents that can be used include mixtures of dioctyl sulfosuccinate salt and sodium benzoate, tetramethyl decynediol ethoxylated dialkylphenol, combinations of modified clay and propylene carbonate, hydrogenated castor oil, ethoxylated vegetable oil, dioctyl ester of sodium succinic acid and sodium benzoate, diatomaceous earth, and mixtures of dimethyl hexane and hexyne diol.

The gel material which is used in the invention is essentially a material which has a phase difference L between the controlled shear stress and the resulting shear strain such that tgL is less than or equal to 1.5, preferably less than or equal to 1.2. TgL is the tangent of the L angle (or phase difference). The measurement of L is made by means of a rheometer having a flat fixed plate and a rotating cone above this plate such as the angle between them is less than 10°, preferably 4°. The cone is caused to rotate by means of a controlled speed motor; the rotation is a sinusoidal one, i.e., the torque and the angular displacement change as a sine function with time. This angular displacement corresponds to the hereabove mentioned shear strain; the torque of the controlled speed motor (which causes the angular displacement) corresponds to the hereabove mentioned controlled shear stress.

The gel which may be used in the invention is primarily organic, which means that it has a low water content, generally less than 5% (by weight), preferably less than 3%, more preferably less than 1%. Typically the gel is water soluble or water dispersible.

Generally, the gel which may be used in the invention is a material having a viscosity from 500 centipoise (measurement made with a Brookfield viscometer at 23° C. with a flat plate rotating at 20 round per minute) to 50000 centipoise, preferably between 1000 and 30000 centipoise, and still more preferably between 1 000 and 5 000 centipoise.

According to one embodiment of the invention, the gels which are used in the invention are successful when submitted to the following puncture test: 500 g of a material/gel are placed in a polyvinyl alcohol water soluble bag (having a 50 micron thick wall) and heat sealed. The bag is suspended using a binder clip at which time a dissecting needle (the diameter of which is 0.1 mm) is inserted into the lower third of the bag and withdrawn. The material/gel is observed for 30 minutes to determine leakage. A gel which is successful in the present test shows no leakage and preferably may be used in the invention. A droplet of material may appear on the hole, but no persistent flowing or leakage occurs.

Preferred characteristics of a gel which is appropriate for the invention are (alone or in combination):

The viscosity should be generally between 500 and 50000 centipoise, preferably between 1000 and 30000 centipoise, and still more preferably between 1 000 and 5 000 centipoise (measurement made with a Brookfield machine).

The dispersibility in water should be substantially complete when the gel is subjected to normal agitation in water after a 15-minute interval, preferably after a 10-minute interval.

The gel preferably contains an essentially non-aqueous solvent.

The chemical nature of the enveloping film constituting the bag can vary quite widely. Suitable materials are water soluble (or possibly water dispersible) materials which are insoluble in the organic solvents used to dissolve or disperse the active ingredient (e.g., agrochemical). Specific suitable materials include polyethylene oxide, such as polyethylene glycol; starch and modified starch; alkyl and hydroxyalkylcellulose, such as hydroxymethylcellulose, hydroxyethylcellulose, hydroxypropyl cellulose; carboxymethylcellulose; polyvinylethers such as poly methyl vinylether or poly(2-methoxyethoxyethylene); poly(2,4-dimethyl-6-triazinylethylene; poly(3-morpholinyl ethylene); poly(N-1,2,4-triazolylethylene); poly(vinylsulfonic acid); polyanhydrides; low molecular weight melamine-formaldehyde resins; low molecular weight urea formaldehyde resins; poly(2-hydroxyethyl methacrylate); polyacrylic acid and its homologs.

A preferred enveloping film comprises or is made from polyvinylalcohol (PVA). When PVA is used, it is preferably partially or fully alcoholyzed or hydrolyzed, e.g., 40–100%, preferably 80–99% alcoholyzed or hydrolyzed, as a polyvinyl acetate (or other ester) film. Copolymers or other derivatives of such polymers can also be used.

Additional preferred materials for constituting the bags in the invention are polyethylene oxide, methylcellulose, and polyvinylalcohol.

The following features, alone or in combination, constitute additional preferred features of the invention:

According to another feature, the gels and the bag containing gel of the invention preferably have a density greater than 1, preferably greater than 1.1.

According to another feature the gels contained in the bags of the invention preferably have spontaneity (as hereafter defined) less than 75, preferably less than 25.

According to another feature, the bags of the invention generally have a capacity of from 0.01 to 12 liters; preferably they have a capacity of from 0.2 to 12 liters, more preferably from 0.45 to 6 liters.

According to another feature the bag is preferably made of a polymeric water soluble film. The thickness of this film is generally between about 10 and about 500 microns, preferably between about 20 to about 100 microns.

According to another feature, the bags of the invention when filled to capacity can contain more than 90% gel by volume, preferably more than 95%, and more preferably more than 98% gel.

EXAMPLES

The following examples are given for illustrative purposes and should not be understood as restricting the invention.

In these examples, the Brookfield viscosity was measured, as previously indicated, with a Brookfield viscosimeter which had a flat plate rotating at 20 revolutions per minute. In all of the following examples, the prepared gels had a tgL of between 0.75 and 1.5.

The emulsion stability of the prepared gels is evaluated according to the following method: 1 ml of the gel is mixed with 99 ml water in a 150 ml tube; the tube is inverted 10 times at the rate of 1 complete inversion per second. Rating of the emulsion stability is made by reading the relative amount of phases after 24 hours. The emulsion stability is rated as follows: "excellent" if the amount of emulsion (phase looking like milk) represents 98 to 100% (v/v) of the total, the balance being cream or thin; "good" if the amount of emulsion represents 90 to 98% (v/v) of the total, the balance being mainly cream with no more than 5 ml being thin; "fair" if the amount of emulsion represents 70 to 90% (v/v) of the total, the balance being cream or thin; and "poor" if the total of emulsion represents 70 or less % (v/v) of the total.

The spontaneity is assessed according to the following method: A mixture of 1 ml gel with 99 ml water are put into a 150 ml glass tube which is stoppered and inverted by 180 degrees (upside down). The number of inversions required to completely disperse the gel is called the spontaneity.

EXAMPLE 1

A gel is made by stirring and shaking at 50° C. a mixture of the following ingredients until they are each dissolved or dispersed:

active ingredient: the herbicide 2,4-D: phenoxy benzoic acid (isooctyl ester): 64.8%
solvent: aromatic solvent with flash point of 65° C.: 24.2%
adjuvants:
non ionic/sulfonate blended emulsifier: 4%
calcium alkylbenzene sulfonate: 1%
mixture of dioctylsulfosuccinate salt and sodium benzoate 6%

During stirring, a dissolution or dispersion appears, and thereafter gelation. Gelation increases as the mixture cools to room temperature (20° C.).

The Brookfield viscosity of the gel is 3000 centipoise.

The emulsion stability is "good" according to the above described test.

1100 g of this gel are put in a one-liter bag made of a film of PVA (88% hydrolyzed polyvinyl acetate; cold water soluble; thickness: 55 microns). The bag, which is almost full (about 95% v/v), is hot sealed. The density of the gel and of the bag containing the gel is 1.1.

The bag is dropped 10 times from 1.2 m above the ground. No breaking or leakage is observed.

The bag is put into a tank containing water under gentle agitation (that is to say such as that obtained with pump recycling). The bag and its contents are dispersed within a 3 minute interval. There is no clogging in the filter, which is a screen having 0.28 mm openings.

EXAMPLE 2

The procedure of Example 1 is repeated, using the same active ingredient in a mixture containing the following adjuvants:

non ionic/sulfonate blended emulsifier: 5.2%
tetramethyl decynediol: 30%

The Brookfield viscosity of the gel is 3000 centipoise.

The emulsion stability is good using the above described test.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 3 minutes interval. There is no clogging in the filter which is a screen having 0.28 mm openings.

EXAMPLE 3

The procedure of Example 1 is repeated, using the same active ingredient in a mixture containing the following adjuvants:

non ionic/sulfonate blended emulsifier: 21.5%
calcium alkylbenzene sulfonate: 3.7%
ethoxylated dialkylphenol: 10%

The Brookfield viscosity of the gel is 3000 centipoise.

The emulsion stability is good using the above described test.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 3 minutes interval. There is no clogging in the filter which is a screen having 0.28 mm openings.

EXAMPLE 4

A gel is made by stirring at 50° C. a mixture of:
active ingredient: bromoxynil acid in the form of an octanoate ester: 61.15%
solvent: aromatic solvent with a flash point of 38° C.: 22.85%
polyaryl phenolethoxylated: 6%
calcium alkylbenzene sulfonate: 2%
clay which has been modified by addition of methyl groups: 6%
propylene carbonate (activating the thickener): 2%

These materials are mixed together while shearing with an attritor mixer. The product started to gel within a few minutes.

The Brookfield viscosity of the gel is 4200 centipoise.

The emulsion stability is good using the above described test.

The spontaneity is 38.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 10 minutes interval. There is no clogging in the filter which is a 50 mesh screen.

EXAMPLE 5

The procedure of Example 4 is repeated, using a mixture containing the following components:
active ingredient:
bromoxynil octanoate: 18.65%
bromoxynil heptanoate: 13.85%
methyl chloropropionic acid (isooctyl ester 37.4%
solvent: aromatic solvent with a flash point of 38° C.: 11.1%
hydrogenated castor oil: 3%
ethoxylated vegetable oil: 3%
non ionic/sulfonate blended emulsifier: 13%

These materials are mixed together while shearing with an attritor mixer. The product started to gel within a few minutes.

The Brookfield viscosity of the gel is 3150 centipoise.

The emulsion stability is good using the above described test.

The spontaneity is 20.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 10 minutes interval. There is no clogging in the filter which is a screen having 0.28 mm openings.

EXAMPLE 6

The procedure of Example 5 is repeated using a mixture containing the following components:
active ingredient:
bromoxynil octanoate: 18.4%
bromoxynil heptanoate: 14%
methyl chloropropionic acetic acid (isooctyl ester) 36.6%
non ionic/sulfonate blended emulsifier: 9%
sodium sulfonate of naphthalene formaldehyde condensate: 3%
dioctyl ester of sodium sulfosuccinic acid and sodium benzoate 2%
diatomaceous earth: 17%

These materials are mixed together while shearing with an attritor mixer. The product started to have the appearance of a smooth paste, and is a gel within a few minutes.

The Brookfield viscosity of the gel is 9000 centipoise.

The emulsion stability is good using the above described test.

The spontaneity is 9.

1100 g of this gel are put in a 1 liter bag made of a film of PVA (88% hydrolyzed polyvinyl acetate; cold water soluble; thickness: 55 microns).. The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 10 minutes interval. There is no clogging in the filter which is a screen having 0.28 mm openings.

EXAMPLE 7

The procedure of Example 5 is repeated, using a mixture containing the following components:
active ingredient:
bromoxynil octanoate: 18.89%
bromoxynil heptanoate: 12.59%
atrazine 44.58%
solvent: same as in example 5 18.54%
amine salt of alkylarylsulfonate: 2.7%
polyethylene glycol: 2.7%

These materials are mixed together while shearing with an attritor mixer. The product started to have the appearance of a smooth paste, and is a gel within a few minutes.

The Brookfield viscosity of the gel is 7300 centipoise.

The emulsion stability is good using the above described test.

The spontaneity is 15.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 10 minutes interval. There is no clogging in the filter which is a screen having 0.28 mm openings.

EXAMPLE 8

The procedure of Example 7 is repeated, using a mixture containing the following components using:
active ingredient:
bromoxynil octanoate: 33.7%
methyl chloropropionic acetic acid (isooctyl ester) 36.2%
solvent: solvent:aromatic solvent with a flash point of 65° C. 3%
non ionic/sulfonate blended emulsifier: 8.5%
calcium dodecyl benzene sulfonate: 1%
tetramethyl decyne diol: 17.6%

These materials are mixed together while shearing with an attritor mixer. The product started to have the appearance of a smooth paste, and is a gel within a few minutes.

The Brookfield viscosity of the gel is 2200 centipoise.

The emulsion stability is good using the above described test.

The spontaneity is 14.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 5 minutes interval. There is no clogging in the filter which is a screen having 0.28 mm openings.

EXAMPLE 9

The procedure of Example 8 is repeated, using a mixture containing the following components:
active ingredient and solvent are the same as in example 8, and amount of active ingredient is the same
solvent is the same but the amount is 10.6%
calcium dodecyl benzene sulfonate: 2%
mixture of dimethyl hexane and hexyne diol: 11.5%
calcium alkylaryl sulfonate and a polyarylphenol ethoxylate: 6%

These materials are mixed together at 90° C. while shearing with an attritor mixer. The product started to have the appearance of a smooth paste, and is a gel within a few minutes.

The Brookfield viscosity of the gel is 2500 centipoise.

The emulsion stability is good using the above described test.

The spontaneity is 5.

1100 g of this gel are put in a 1 liter bag made of a file of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 5 minutes interval. There is no clogging in the filter which is a screen having 0.28 mm openings.

EXAMPLE 10

The procedure of Example 5 is repeated, using a mixture containing the following components using:

active ingredient:
bromoxynil octanoate: 33.5%
bromoxynil heptanoate: 33.5%
solvent: aromatic solvent with a flash point of 65° C.: 22.75%
non ionic/sulfonate blended emulsifier: 4.5%
calcium dodecyl benzene sulfonate: 1%
mixture of dioctyl sodium sulfosuccinate and sodium benzoate: 4.25%
tetramethyl decyne diol: 0.5%

These materials are mixed together at 50° C. while shearing with attritor mixer. The product started to have the appearance of a smooth paste, and is a gel within a few minutes.

The Brookfield viscosity of the gel is 4850 centipoise. The emulsion stability is excellent using the above described test.

The spontaneity is 10.

1100 g of this gel are put in a 1 liter bag made of a film of PVA (88% hydrolyzed polyvinyl acetate; cold water soluble; thickness: 55 microns). The bag, which is almost full (about 95% v/v), is hot sealed. The density both of the gel and of the bag containing the gel is 1.1.

The bag is then dropped 10 times from 1.2 m upon the ground. No breaking or leakage is observed.

The bag is placed in a tank containing water under gentle agitation (that is to say such as that obtained with pump recycling). It is dispersed within a 3 minutes interval. There is no clogging in the filter which is a screen having 0.28 mm openings.

What is claimed is:

1. A containerization system for holding and securing hazardous chemical compounds which comprises a water soluble or water dispersible bag which completely encloses a water soluble or water dispersible gel, said gel comprising a hazardous chemical compound, wherein said gel possesses a viscosity of between about 1,000 and 30,000 centipoise.